US 11,464,895 B2

(12) United States Patent
Charlez (10) Patent No.: US 11,464,895 B2
(45) Date of Patent: Oct. 11, 2022

(54) BODY DRAINAGE APPARATUS (71) Applicant: THORAGEN AB, Solna (SE)

(72) Inventor: Mikael Charlez, Mölndal (SE)

(73) Assignee: Thoragen AB, Solna (SE)

( * ) Notice: Subject to any disclaimer, the term of this patent is extended or adjusted under 35 U.S.C. 154(b) by 520 days.

(21) Appl. No.: 16/311,990

(22) PCT Filed: Jun. 22, 2017

(86) PCT No.: PCT/SE2017/050696
§ 371 (c)(1),
(2) Date: Dec. 20, 2018

(87) PCT Pub. No.: WO2017/222465
PCT Pub. Date: Dec. 28, 2017

(65) Prior Publication Data
US 2019/0240382 A1 Aug. 8, 2019

(30) Foreign Application Priority Data
Jun. 23, 2016 (SE) .................... 1650908-5

(51) Int. Cl.
A61M 1/00 (2006.01)

(52) U.S. Cl.
CPC ............ A61M 1/74 (2021.05); A61M 1/0001 (2013.01); A61M 1/73 (2021.05); A61M 2205/15 (2013.01); A61M 2205/3351 (2013.01)

(58) Field of Classification Search
CPC .............. A61M 1/0031; A61M 1/0025; A61M 1/0001; A61M 1/006; A61M 2205/15;
(Continued)

(56) References Cited

U.S. PATENT DOCUMENTS 5,135,485 A * 8/1992 Cohen ................. A61M 5/1684
324/606
5,267,956 A 12/1993 Beuchat
(Continued)

FOREIGN PATENT DOCUMENTS

CA 2884773 A1 3/2014
EP 2821758 A1 1/2015
(Continued)

OTHER PUBLICATIONS

Written Opinion dated Jan. 30, 2018 issued in International Application No. PCT/SE2017/050696.
(Continued)

Primary Examiner — Jessica R Arble
(74) Attorney, Agent, or Firm — Renner, Otto, Boisselle & Sklar, LLP (57) ABSTRACT A body drainage system for draining fluid from a body cavity of a patient, the body cavity being provided with an access port, wherein the system includes:
  a peristaltic pump mechanism,
  a housing for housing at least a portion of the peristaltic pump mechanism,
  a flexible tube configured to be connected at an access port end to the patient access port, and at a collection unit end to a collection unit,
  a pre-chamber connected to the flexible tube arranged to receive fluid via the flexible tube,
  a processor,
wherein the pre-chamber is provided with a pressure sensor and the processor is configured to receive pressure signal from the pressure sensor to be able to detect air leakage and/or to calculate the amount of air leakage.

19 Claims, 8 Drawing Sheets (58) Field of Classification Search
CPC .......... A61M 2205/3351; A61M 60/279; A61J 1/10; A61J 1/2093
See application file for complete search history.

(56) References Cited

U.S. PATENT DOCUMENTS

| | | | | |
|---|---|---|---|---|
| 2003/0136181 A1* | 7/2003 | Balschat | ............. | A61M 1/1601 73/40.5 R |
| 2007/0265594 A1* | 11/2007 | Hagermark | ........... | A61M 1/167 604/410 |
| 2010/0049134 A1* | 2/2010 | Schuman, Jr. | .......... | A61M 1/71 604/153 |
| 2011/0015593 A1 | 1/2011 | Svedman | | |
| 2012/0046623 A1* | 2/2012 | Bordeau | ............... | A61F 5/4405 604/317 |
| 2012/0184932 A1* | 7/2012 | Giezendanner | ..... | A61M 1/0025 604/319 |
| 2013/0144227 A1* | 6/2013 | Locke | .................... | A61M 1/98 604/319 |
| 2013/0261539 A1* | 10/2013 | King | .................... | G01F 23/265 604/65 |
| 2013/0267779 A1 | 10/2013 | Woolford | | |
| 2014/0336602 A1 | 11/2014 | Karpowicz et al. | | |
| 2015/0025482 A1 | 1/2015 | Begin | | |
| 2015/0133829 A1 | 5/2015 | Debusk et al. | | |
| 2015/0164690 A1* | 6/2015 | Peterson | ............. | A61M 1/0058 604/67 |
| 2015/0246164 A1* | 9/2015 | Heaton | ................... | A61M 1/74 604/313 |
| 2015/0297405 A1 | 10/2015 | Bourne | | |

FOREIGN PATENT DOCUMENTS

| | | |
|---|---|---|
| WO | WO 1993/015777 | 8/1993 |
| WO | WO 2013/078214 | 5/2013 |

OTHER PUBLICATIONS

International Search Report dated Jan. 30, 2018 issued in International Application No. PCT/SE2017/050696.
Swedish Search Report dated Dec. 14, 2016 issued in Swedish Application No. 1650908-5.

* cited by examiner

BODY DRAINAGE APPARATUS

RELATED APPLICATIONS

This application is a national phase entry of International Application No. PCT/SE2017/050696 filed on Jun. 22, 2017 and published in the English language, which claims priority to Swedish Application No. 1650908-5 filed on Jun. 23, 2016, both of which are hereby incorporated by reference.

TECHNICAL FIELD

The present invention relates generally to a drainage apparatus and a method for drainage of excess body fluid from a body cavity of a patient.

BACKGROUND

In contemporary medical care, the movement of fluid from a body cavity to another point for collection is a routine need and can be performed in a number of ways. When tubing or piping is used for carrying the fluid during the movement either gravity or a pump is utilized to create and/or sustain a suction pressure needed to move the fluid from one point to another.

SUMMARY OF THE INVENTION

At times the movement of fluid from the body must be performed in a gentle, slow and steady manner. Such gentle, slow and steady manner can be designated "peristalsis". Peristaltic pumping may be performed in a number of ways including, but not exclusively, by hand pump or with the use of a peristaltic pump.

In medical care, drainage procedures are typically performed by hand pumping, to achieve the peristaltic movement of excess fluid in a patient's body into drainage bags for disposal or into syringes for laboratory analysis or any other medical use. Hand pumping is time consuming and requires a person to be in attendance at all times. Further, the attendant must manually perform the hand pumping necessary to sustain the peristaltic movement. It is difficult to generate consistent suction forces using hand pumping.

Additional known methods for drainage procedures include plastic vacuum suction bottles and wall/portable suction. These methods typically produce a constant suction rather than a peristaltic suction. These methods also include plastic bottles that are pre-assembled with a vacuumed pre-set under pressure causing inadequate suction; are bulky and causing storage, operational and shipping difficulties; typically, they are limited in size necessitating frequent changes during the procedure; require special medical waste handling procedures; and when shattered in use create the danger of contamination problem of body fluids. Wall suction, in addition to providing only constant suction, is not readily available in all clinical settings. Wall units tend to create greater suction forces than what is safe for a normal drainage procedure.

Generally, there is provided an apparatus and a method for collection of a bodily fluid, the apparatus comprises a peristaltic pump device and the method comprises steps for the regulation and control of the peristaltic pump movements and collection of the bodily fluid.

Thus, there is provided an apparatus incorporating a peristaltic pump device and a method for the regulation and control of peristaltic movement and measurement of bodily fluid volume and detection of potential air leakage.

According to a first aspect of the invention there is provided a drainage apparatus for aspirating and measuring of body fluids, the apparatus comprising a peristaltic pump device for a pressure controlled peristaltic movement regulation of fluid transportation comprising: a peristaltic pump housing and a peristaltic mechanism unit arranged in the peristaltic housing and a fluid collection bag being able to be secured releasable on the peristaltic pump housing. The drainage apparatus is arranged to drain the fluid through tubing connected to the patient and said tubing is in a distal end connected to a rigid pre-chamber that is arranged just before the peristaltic pump in the direction of fluid. The inside of the pre-chamber stands in contact with a pressure sensor located near the rigid pre-chamber for the purpose of measuring the pressure and supply pressure readings to the processor for controlling the peristaltic pumping mechanism by comparing the current suction pressure with a pre-set desired suction pressure and pause pumping if the desired suction pressure is reached. Further, the processor is configured to estimate the amount of air-leakage by using readings from the pressure sensor to determining the level of air leakage by pausing pumping and measuring a pressure drop time interval of a pressure drop from an initial pressure to a second pressure inside the pre-chamber. The rigid pre-chamber is arranged to have a fixed known volume to facilitate calculations. Alternately, or additionally, the processor may be configured to pause the peristaltic pump for a predetermined time and to calculate an air-leakage value based on a measured pressure drop during the predetermined time, and also based on the fixed volume of the pre-chamber.

The collection bag is arranged to be made of a soft material. It is provided with an arrangement of multiple disposable screen-printed capacitive filling-level sensors preferably arranged on the innermost backside of the said collection bag for the purpose of detecting a filling level in the fluid collection bag. The capacitive filing sensors may also comprise a connector for connecting an electrical cable that transfers the capacitive signals from the bag to the processor.

According to a second aspect of the invention there is provided a method of utilizing a regulated peristaltic pumping mechanism to avoid the need of a negative pressure inside a collection unit. An advantage is that this enables the possibility to use a soft collection bag instead of a rigid airtight canister. Said soft collection bag will also expand in the presence of air-leakage and hence serve as an indirect air-leakage indicator. Potential over-pressure will be released though a de-air-venting valve.

According to a third aspect of the invention there is provided a method utilizing a pressure sensor as means for detecting air leakage inside a closed system of tubing, pre-chamber and peristaltic pump by measuring the time for a certain pressure drop in a pre-chamber of known volume.

BRIEF DESCRIPTION OF THE DRAWINGS

In order that the manner in which the above recited and other advantages and objects of the invention are obtained will be readily understood, a more particular description of the invention briefly described above will be rendered by reference to specific embodiments thereof which are illustrated in the appended drawings.

Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Figures 1, 2A, 2B:
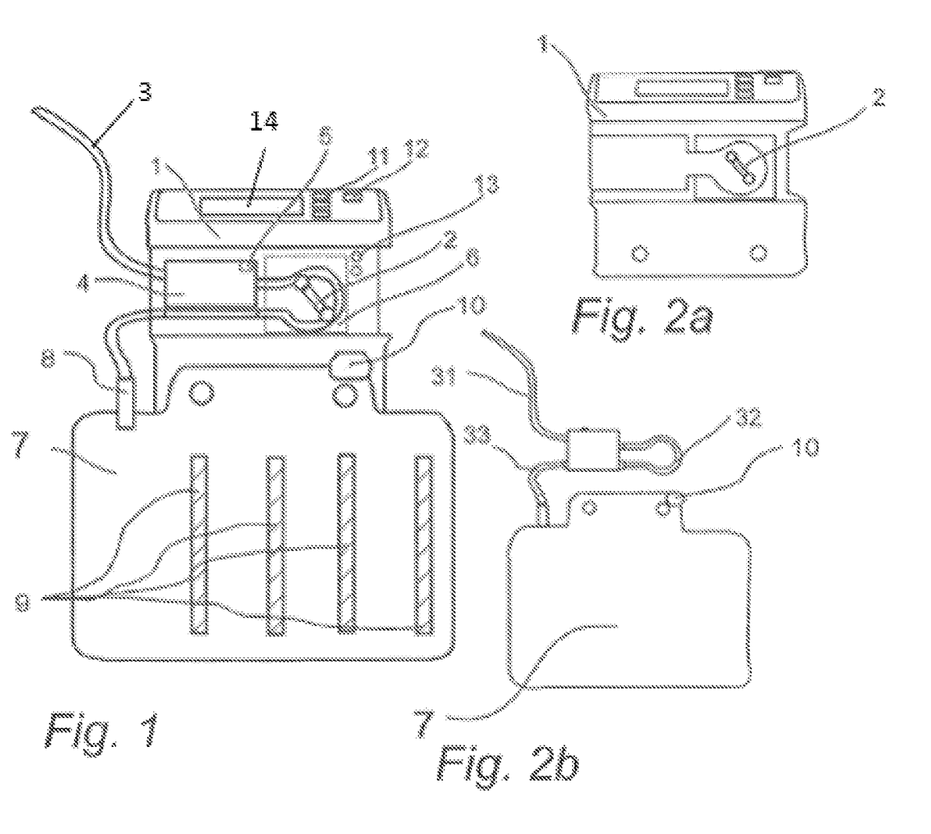
FIG. 1 shows a front view of a drainage system according to an embodiment of the invention.
FIG. 2a shows a front view of a base unit of the system of FIG. 1
FIG. 2b shows a front view of a disposable drainage tube unit and collection bag of the system of FIG. 1.

FIG. 1 shows an embodiment of a drainage system for draining excess body fluid from a patient. The system comprises a housing 1 that houses a peristaltic mechanism 2, a patient drainage tube 3, a pre-chamber 4 and a collection bag 7. From FIG. 2a and FIG. 2b it can be seen that the system can be divided into a base unit comprising the housing with the peristaltic mechanism, electronics and display 14, and, as shown in FIG. 2b, a disposable drainage tube unit 3, 4, 31, 32, 33 and a disposable collection bag 7. The pre-chamber 4 is preferably configured to be inserted into a recess of the housing 1. The recess is configured to receive and to hold the pre-chamber, preferably by the aid of a snap-lock mechanism.

The patient drainage tube 3 have a first portion 31 connected to the pre-chamber for conducting fluid from the patient to the pre-chamber 4. The patient drainage tube 3 has a second portion 32 connected to the pre-chamber and preferably configured in a loop to fit around the peristaltic rotor 2. Preferably the second portion 32 of the patient drainage tube 3 transitions into a third portion 33 having a connector for connecting it to the collection bag 7. The second portion 32 of the patient drainage tube is made to have a certain length to make it possible to arrange in a loop around the rotor of the peristaltic mechanism 2. The patient drainage tube 3 is devised to be inserted through the peristaltic mechanism 2 and the housing is arranged to provide holding means to hold the second portion 32 of the patient drainage tube 3 in its operating position through a hatch 6 that in its closed position secure the operating position of said patient drainage tube 3 and to stabilize for optimal operating peristaltic conditions.

The apparatus housing 1 is provided with indicator means 13 to allow inspection of a battery indicator 13 in order to check if the apparatus is appropriately charged. When the apparatus is operated by a user, the hatch 6 is placed in its open position and the second portion of the patient drainage tube 3 is inserted in its operating position in the peristaltic mechanism 2 and then secured in the peristaltic mechanism 2 by closing the hatch 6. The collection bag 7 is then connected to the collection bag end of the second portion of the patient drainage tube 3.

As the patient drainage tube 3 and the rigid pre-chamber 4 are in position the apparatus is configured to be activated by pushing the power on button 12 in order to make the apparatus ready for connection to a patient's access port.

The housing is provided with a peristaltic regulator button 11. Pressing the peristaltic regulator button 11 activates the drainage procedure and the peristaltic pumping is guided and controlled with the aid of the peristaltic regulator 11. As the bodily fluid is drained from the bodily cavity it enters the first portion of the patient drainage tube 3, pre-chamber 4 and the second portion of the patient drainage tube 3 in the peristaltic mechanism 2 and then finally the body fluid enters the collection bag 7.

The peristaltic regulator 11 is configured to control the peristaltic motor in a pre-set manner by automatically or by operator input setting a desired negative pressure. The peristaltic regulator 11 may be a separate unit or configured as part of a processor 105 as shown in FIGS. 5a and 5b.

Figure 5A:
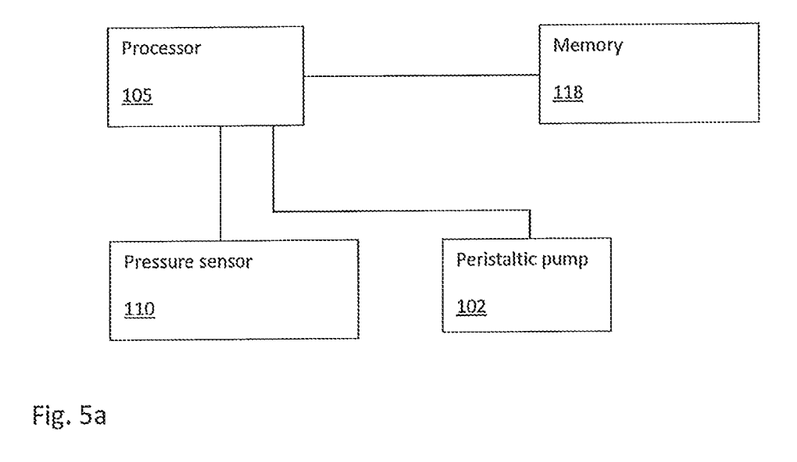
FIG. 5a shows a block diagram of a drainage system according to an embodiment of the invention.

FIG. 5a shows a block diagram of a drainage system according to an embodiment of the invention. A processor 105 is connected to a memory 118, to a pressure sensor 110 for sensing the suction pressure created by a peristaltic pump 102.

Figure 5B:
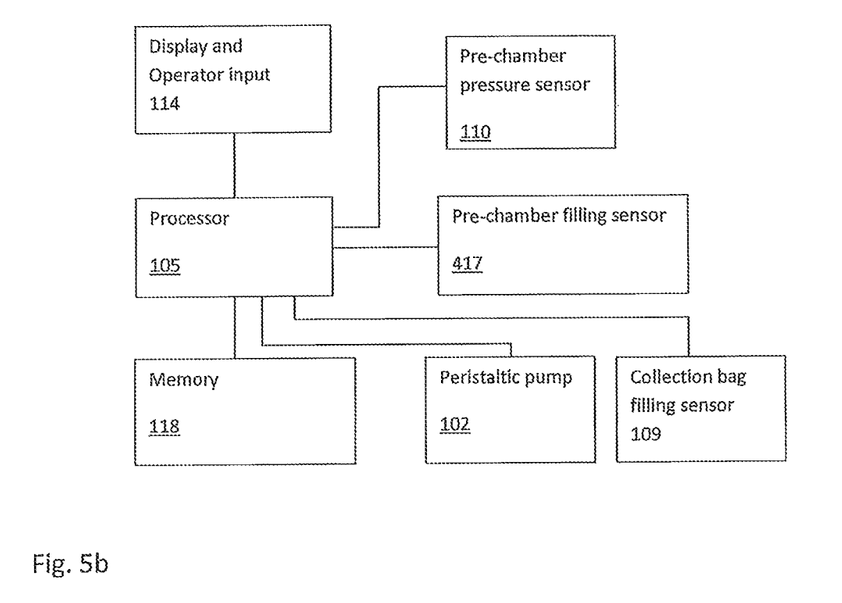
FIG. 5b shows a block diagram of a drainage system according to a further embodiment of the invention.

FIG. 5b shows a block diagram of a drainage system according to a further embodiment of the invention. A processor 105 is connected to a memory 118, to a pre-chamber pressure sensor 110 for sensing the suction pressure created by a peristaltic pump 102. Further the processor is connected to a display an operator input unit 114 for displaying volumes and pressure and process information such as battery level and on/off status for the apparatus and/or for the peristaltic pump. Still further the processor is connected to one or more collection bag filling sensors 109 to receive information on amount of drained volume. Even still further the processor is connected to one or more pre-chamber filling sensors to receive information to be able to calculate an amount of air leakage during pump pause, see FIG. 6 and below.

The pressure sensor 5, 110 measures the pressure inside the pre-chamber 4 and provides information to be shown to the user on the display 14, 114. The peristaltic mechanism is rotating and the processor 105 controls the rotating rate based on information from the pressure sensor 5. If the battery power supply reaches critical levels, the battery power indicator 13 alerts the user to recharge the battery.

Figure 3:
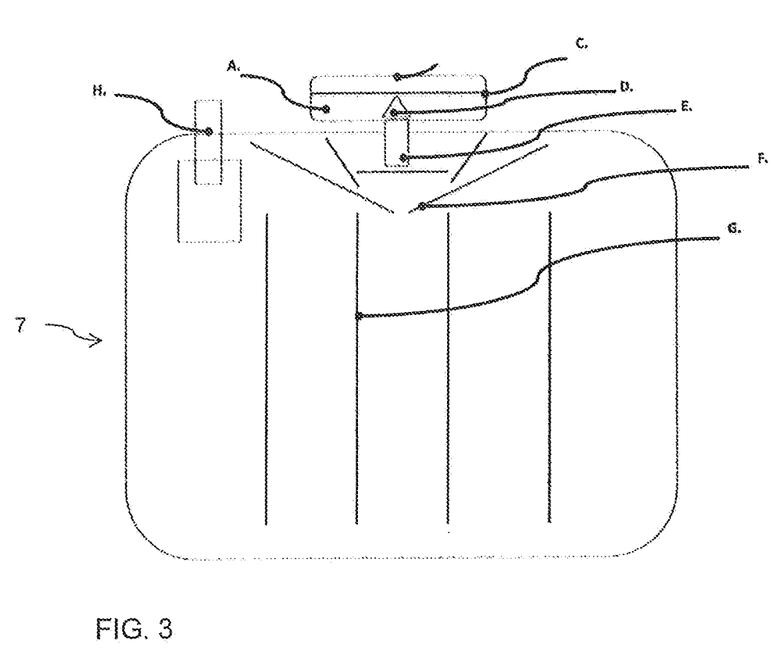
FIG. 3 shows a schematic front view of a collection bag.

Now referring to FIGS. 1 and 3, the collection bag 7 is manufactured in a flexible material and are provided with attachment means to allow the bag 7 to be attached to the housing 1 in a hanging manner. The collection bag is also provided with one or more filling sensors 9 for sensing the level of liquid in the bag 7. The filling sensors are preferably of a disposable flexible capacitive type such as screen printed disposable sensors. The sensors 9 may be directly attached or printed on an inner or outer surface of the collection bag. The sensors 9 may as an alternative, or additionally, be attached or printed on a foil, which are affixed inside the hollow of the collection bag. The one or more filling level sensors (9) may as an alternative or additionally be arranged in an area where the pressure is atmospheric or over atmospheric.

As liquid is gathered in the collection bag 7, the liquid affect the disposable screen-printed capacitive filling sensors 9. The sensors will sense the changed capacitance and a capacitive signal is conducted from the filling sensors to the microprocessor via a connector 10 arranged on the collection bag 7, and a cable preferably completely hidden inside the housing 1. In an embodiment, the capacitive connector 10 is releasably secured to the housing 1 via a magnetic arrangement. Further, the processor 105 uses the sensor signals to calculate the filling level volume. The volume is subsequently presented on the display unit 14. The screen-printed filling sensors 9 could preferably be of a selected electroplated oxidase/graphite pads type, based on capacitive sensor technology.

Now referring to FIGS. 1, 4, 6 and 7, the apparatus is provided with means for detecting air leakage. Air leakage is detected by measuring 620, via the pressure sensor 5, the pressure drop over time inside the pre-chamber 4. The pressure sensor 5 is preferably arranged at the ceiling of the pre-chamber 4, or standing in communication with the inner of the pre-chamber via a short air-channel. The processor is configured to make a temporary stop or pause 625 in the peristaltic operating procedure by inactivating the pumping mechanism. In case there is an air leakage the suction pressure inside the pre-chamber will decrease. The pressure inside the pre-chamber is monitored 635. The pressure alteration is detected by the pressure sensor 5 and as the volume of the pre-chamber 6 is known, the processor can calculate the estimated air leakage based on factors of time and pressure drop in the known volume of the pre-chamber 4.

Figure 7:
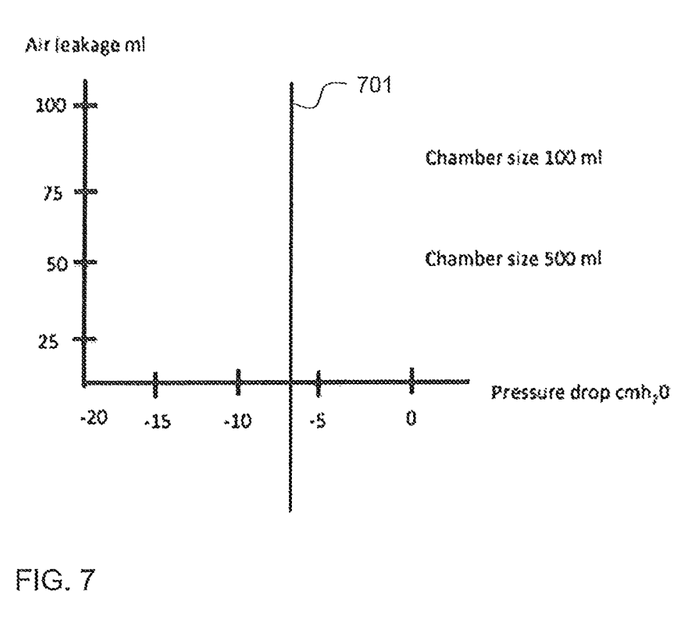
FIG. 7 shows a diagram of air leakage as a function of pressure drop during a fixed time for two different sized pre-chambers.

FIG. 7 shows a diagram of air leakage as a function of pressure drop during a fixed time for two different sized pre-chambers. The line 701 illustrates how a certain pressure drop can be translated to a certain air leakage in millilitres depending on the pre-chamber size. As two examples chambers sizes of 100 ml and 500 ml are show. Tests have shown that a suitable size (inner volume) of the pre-chamber 4 is in the interval of 100 ml to 500 ml.

Excessive volume of air gathering in the collection bag is evacuated through a de-air-vent-housing (A) provided at the collection bag 7, see FIG. 3. The bag is provided with a filtered air mechanism to safely let air leave the bag. The filtered air mechanism is prevented from being occluded by bodily fluid by means of a duck-valve (D) and a welded pattern (F) onto/into said collection bag (7) arranged as a liquid trap.

Figure 4:
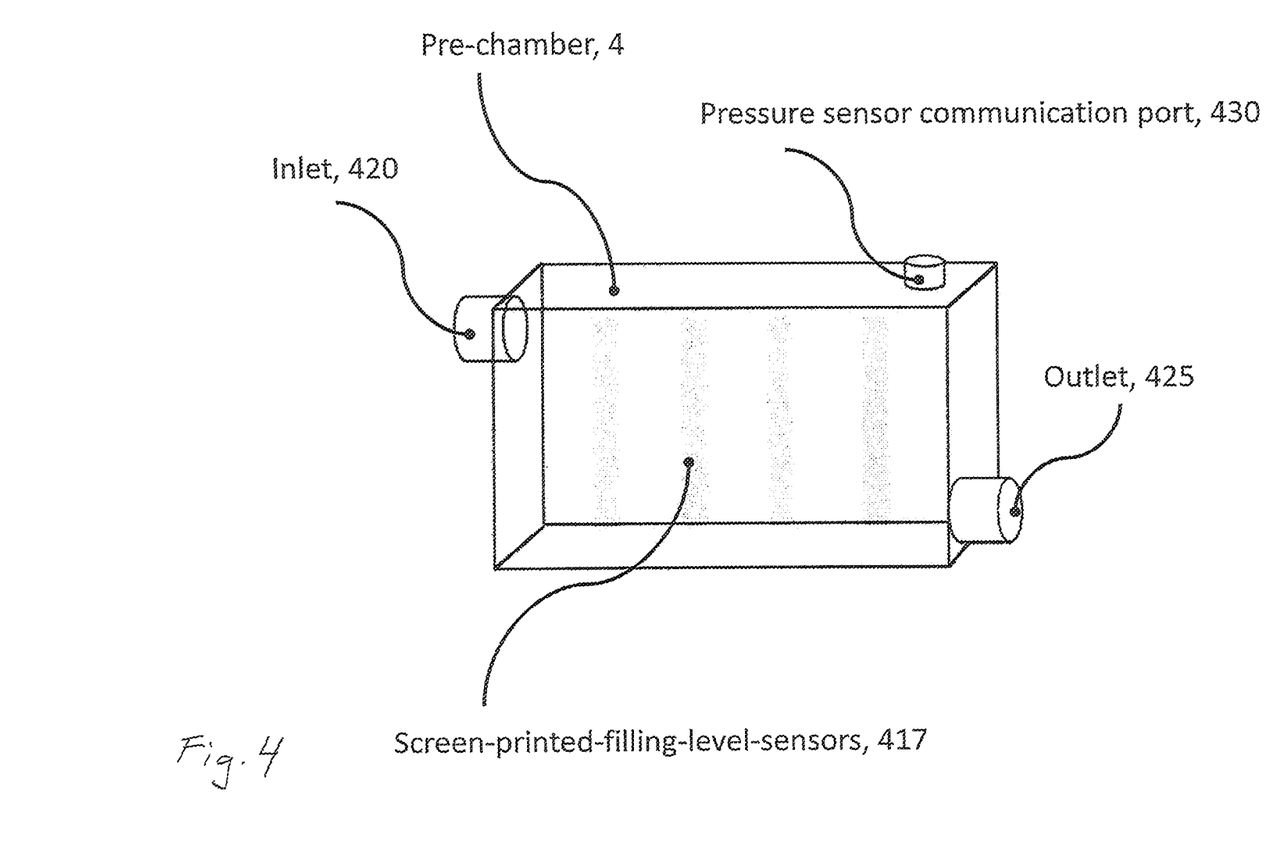
FIG. 4 shows a detail front view of a pre-chamber according to an embodiment of the invention.
Figure 6:
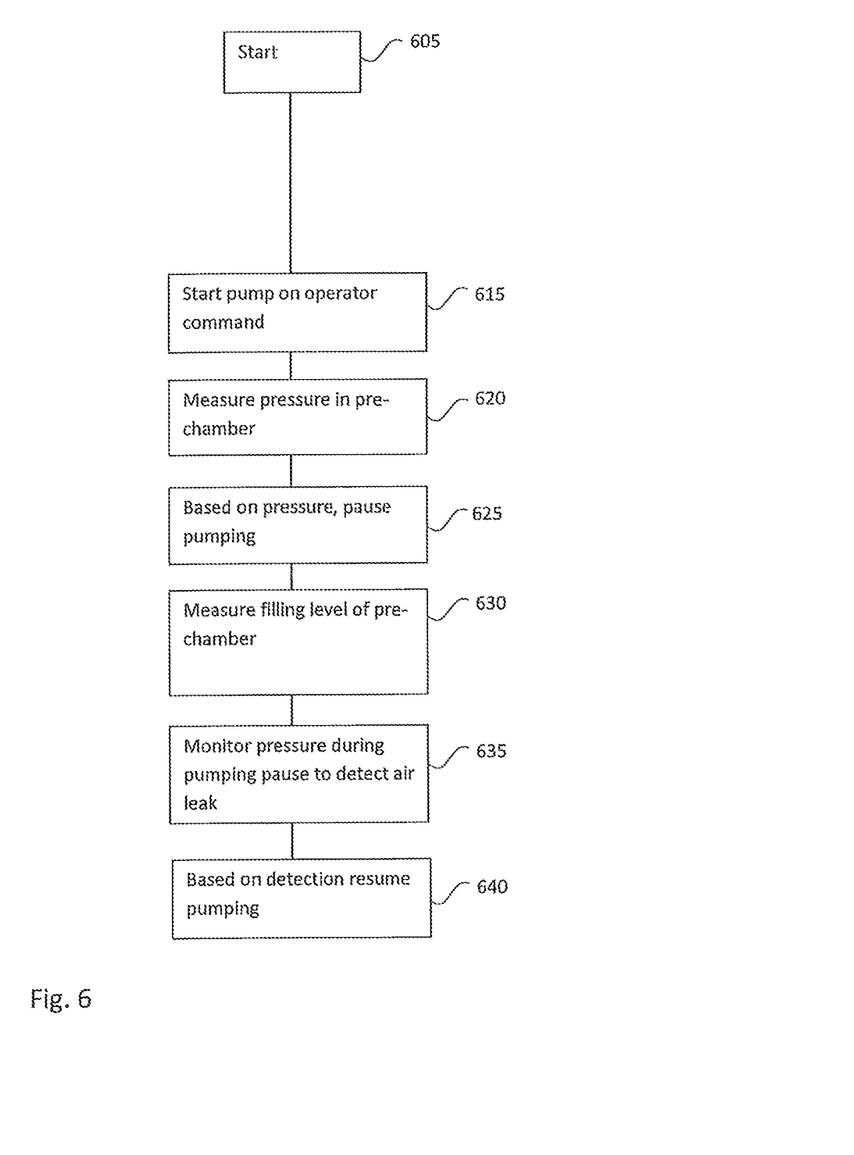
FIG. 6 shows a flow chart of a method for detecting air leakage with the aid of the drainage system of FIG. 1.

Now referring to FIG. 4 and FIG. 6, an arrangement of sensors 417 are preferably attached on the outside of the pre-chamber 4 for measuring 630 the filling level of the pre-chamber and thus detecting if there is a reduced dead space and subsequently to allow for compensation for such reduced dead space during air leakage measurement. The sensors are preferably of a disposable, screen-printed type. As an alternative, the sensors may be applied on a foil and fixed inside the hollow of the pre-chamber 4.

Now referring to FIG. 3, the collection bag (7) may further be provided with an arrangement of splash guards (G) in order to hold the liquid firmly in position against the liquid filling sensors (9) shown in FIG. 9. The splash guards (G) are preferably arranged as one or more vertical weldings or one or more vertical lines of tight junction between opposing inner surfaces of the collection bag 7. Each line of tight junction extends over a major portion of the height of the collection bag. Preferably, the weldings or tight junctions are arranged not to extend to the bottom of the bag leaving horizontal openings at the bottom of the collection bag 7 to allow liquid to fill the bag evenly, and at the top to allow air to evacuate.

Furthermore, the collection bag is provided with a venting house A in order to let out air trapped in the collection bag during drainage procedure. The venting house is provided with a duck valve (D) and an arrangement of liquid trap (F) in order to prevent liquid from entering the venting house A.

The foregoing description of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of this invention as defined by the accompanying claims.

EVF Sensor

Figure 8A:
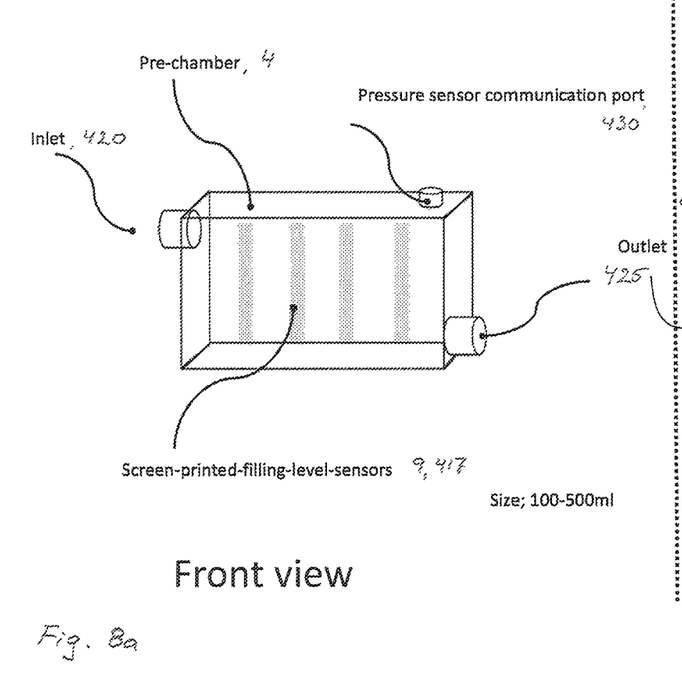
FIG. 8a and FIG. 8b shows the pre-chamber of FIG. 4, wherein the system is further provided with an optical sensor for measuring erythrocyte volume concentration in the drainage fluid.
Figure 8B:
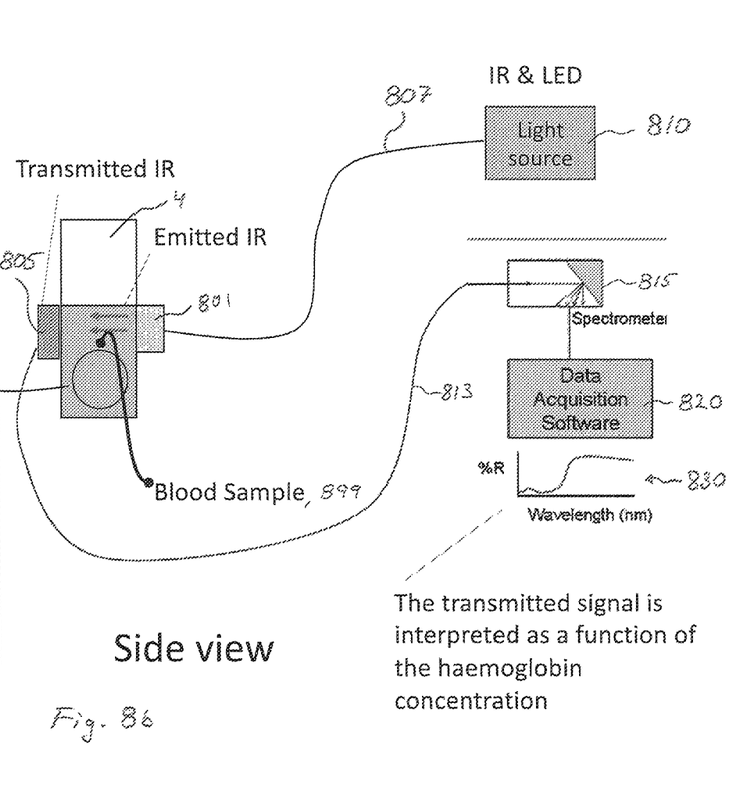

The drainage system may further be provided with an integrated device to measure the erythrocyte volume fraction (EVF) of the drainage fluid. The drainage fluid may comprise blood. FIG. 8a and FIG. 8b shows the pre-chamber 4 of FIG. 4, manufactured in a transparent material, wherein the drainage system further is provided with an optical sensor system 810, 801,805, 807, 813, 815, 820, 830 for measuring erythrocyte volume concentration or fraction in the drainage fluid.

Now turning to FIGS. 8a and 8b, such a drainage system with an EVF measuring function may preferably be provided with a light source 810 arranged to provide infrared and/or near infrared light to the fluid present in the pre-chamber 4. The light source 810 may be arranged at a distance from the pre-chamber 4, and the light conducted to a light emitting unit 801 which is arranged to be in direct contact or very close to the pre-chamber wall when the disposable pre-chamber is fitted. The light is conducted with the aid of a first light conductor 807. The system is preferably provided with an optical light collector unit 805 that collects transmitted light, and is arranged opposite the light emitting unit 801. The transmitted light is conducted to an optical sensor module 815, 820, 830 via a light conductor 807. The optical sensor module is arranged to receive light from the light source transmitted and/or reflected via the drainage fluid. The optical sensor module is configured to provide a signal representative of the concentration of erythrocytes in the drainage fluid. The in this way measured concentration of erythrocytes may be displayed or communicated to a remote monitoring system.

The optical sensor module preferably comprises a spectrometer unit 815, a data acquisition unit 820 and an interpretation/display unit 830 for analysing the spectral content of the received light to be able to interpret the signal as representative of haemoglobin concentration.

Preferably, the optical sensor is a near infrared sensor, preferably working in the wavelength(s) of around 660 nm, and/or 730 nm, and/or 830 nm.

In this way, using preferably an optical sensor such as near infrared reflectance spectroscopy (NIRS) located near the pre-chamber 4 the accumulated whole blood and its influence on erythrocyte volume fraction (EVF) and/or hematocrit values could be determined.

The increase of hemoglobin has a strong influence on the severity of ongoing post-operative-bleeding. Transmitted/reflected light is preferably measured by an integrated optical sensor, which could as an example be working at three wavelengths (660 nm, 730 nm, and 830 nm). The increase of free hemoglobin in the drained fluid would hence lead to a decrease of detected reflected light at all three wavelengths, indicating an increase of EVF and hematocrit values and thereby indicating that a bleeding is more severe.

Figure 9A:
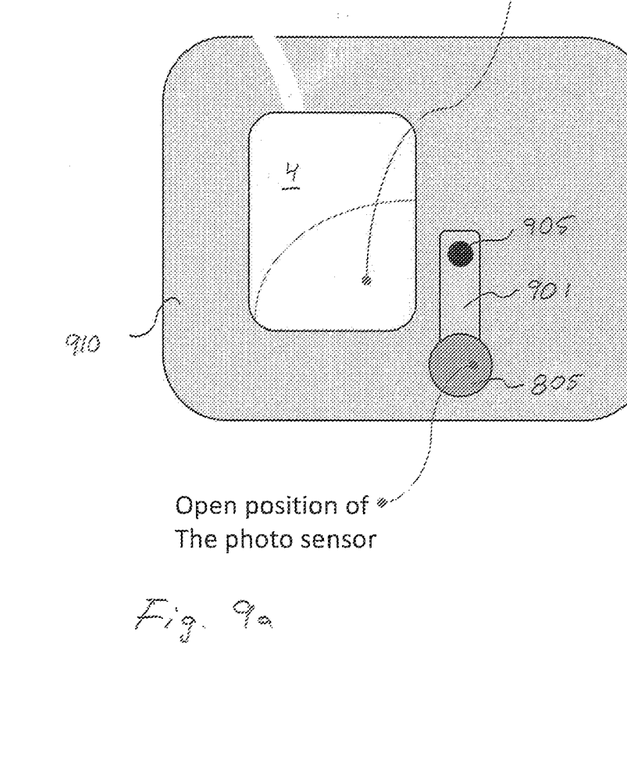
FIG. 9a and FIG. 9b shows a close up of a pre-chamber and a frame of the peristaltic pump housing for mounting the pre-chamber with the aid of a pivotable arm.
Figure 9B:
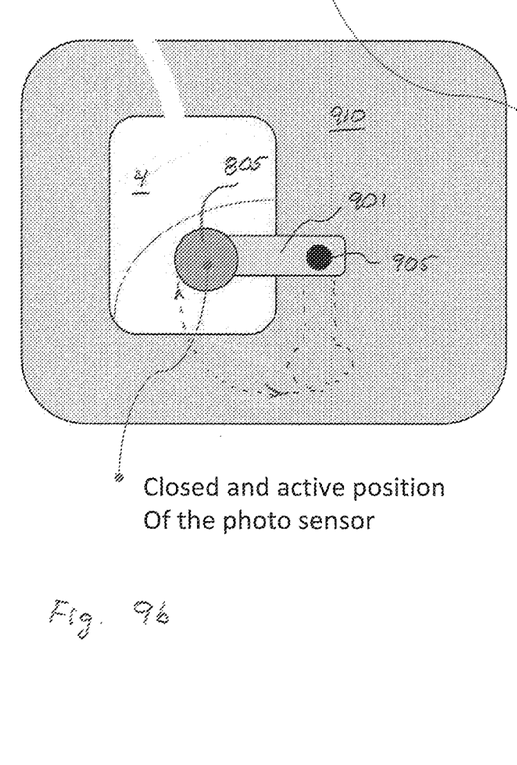
Figure 9C:
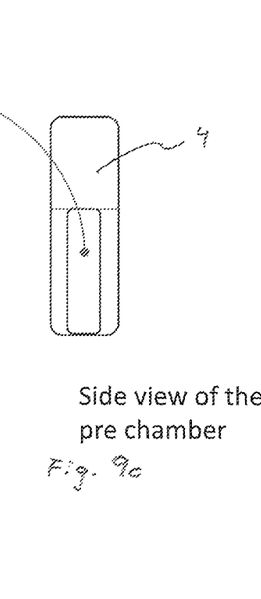
FIG. 9c shows a side view of the pre-chamber.

FIG. 9a and FIG. 9b shows a close up of a pre-chamber 4 and a frame 910 for mounting the pre-chamber 4. The frame 910 is preferably a part or portion of the total peristaltic pump housing 1. The pre-chamber may preferably be configured with a portion of it being formed thinner, having a controlled thickness, facilitating precise measurements performed via the optic sensor. The thinner portion may be in the interval of 25-60% of the nominal thickness of the pre-chamber. Preferably in the interval of 40-50%.

The optic sensor light collecting unit 805 may be arranged at a first end of a pivotable arm 901 hinged at a pivot 905 at the other end of the arm 901.

The arm 901 with the sensor light collecting unit 805 is thus able to swing from an open position, FIG. 9a, to a closed and active position, FIG. 9b. In the open position, a pre-chamber 4 can easily be positioned in the frame 910. In the closed position, the optical sensor light collecting unit 805 becomes in position opposite the light emitting unit 801 (not shown in FIG. 9b) to easily collect light that has passed through the pre-chamber walls of the thinner portion 422, see FIG. 9c, of the pre-chamber 4, and through the drainage fluid 899 collected in the pre-chamber 4. Simultaneously, the arm 901 keeps the pre-chamber in place, preventing it from falling out of position. The arm and pivot 905 are arranged such that the light collector unit, the light emitter unit and the thinner portion of the pre chamber becomes aligned when the arm is swung to the closed position.

As an alternative, the light emitting unit 801 and the light collecting unit 805 are fixed in position and the pre-chamber 4 is slided into position between them either from the front or from the side, the frame 910 then is formed to allow this.

LEGEND

A. Venting house
B. Air outlet
C. Filter
D. Duck-valve
E. Inlet vent
F. Liquid trap
G. Splash-guard
H. Drainage tube collector
1. Housing
2. Peristaltic mechanism
3. Patient drainage tube
4. Pre-chamber
5. Pressure sensor
6. Hatch
7. Collection bag
8. Drainage tube connector
9. Screen-printed liquid filling sensors
10. Filling sensor connector
11. Pressure regulator button
12. Power on button
13. Battery power indicator
14. Display unit
31. Drainage tube first portion
32 Drainage tube second portion
33 Drainage tube third portion
102 Peristaltic pump
105. Processor
109 Collection bag filling sensor
110. Pre-chamber pressure sensor
114 Display and operator input unit
118. Memory
417. Filling level sensors of pre-chamber
420. Pre-chamber inlet
422. Pre-chamber thinner portion
425. Pre-chamber outlet
430. Sensor communication port
801. Light emitting unit
805. Light collecting unit
807. First light conductor
810. Light source
813. Second light conductor
815 Spectrometer
820. Data acquisition unit
830. Interpretation/display unit
899. Blood/drainage fluid
901. Pivotable arm
905. Hinge pivot
910. Frame

The invention claimed is:

1. A drainage system for aspirating and measuring of body fluids, the drainage system comprising:
a peristaltic pump housing and a peristaltic mechanism unit arranged in the peristaltic pump housing;
a fluid collection bag being able to be secured releasably on the peristaltic pump housing;
a rigid pre-chamber arranged to connect a drainage tubing to the collection bag;
a pressure sensor located adjacent the rigid pre-chamber and arranged to be in communication with said pre-chamber for sensing a pressure in the rigid pre-chamber or the purpose of controlling the peristaltic pumping mechanism by a pre-set pressure and to determine the level of air leakage;
a plurality of filling level sensors arranged on a backside of the fluid collection bag for detecting a filling level in the fluid collection bag; and
a processor configured to:
create suction pressure in a tube system for aspirating body fluid by means of the peristaltic mechanism;
measure the suction pressure;
pause the peristaltic mechanism for a predetermined time;
monitor the suction pressure during pumping pause; and
calculate the level of air leakage based on a pressure change during pumping pause, a fixed volume of the rigid pre-chamber, and the predetermined time of pumping pause.

2. The system according to claim 1 wherein the calculating of the level of air leakage is performed by estimating the time of a pressure drop.

3. The system according to claim 1 wherein said filling level sensors comprise a connector element that transfers the capacitive signals from the fluid collection bag to the processor for the purpose of measuring a collected volume.

4. The system according to claim 1 wherein the filling sensors are disposable screen-printed capacitive sensors.

5. The system according to claim 1, wherein the pressure sensor is located outside of the rigid pre-chamber in the peristaltic housing and communicates with the pre-chamber via a communication port.

6. The system according to claim 2, wherein the pressure-drop over time in the pre-chamber is translated to an estimated air leakage though the volume of the pre-chamber.

7. The system according to claim 6, wherein the pre-chamber is provided with capacitive sensors for measuring of a collected volume in the pre-chamber in order to compensate for a reduced dead space in said pre-chamber during an air leakage measurement.

8. The system according to claim 7, wherein the capacitive sensors are disposable screen-printed capacitive sensors.

9. The system according to claim 1, wherein the filling sensors are screen-printed inside the fluid collection bag.

10. The system according to claim 3, in which the connector element is releasably secured to the housing via a magnetic arrangement.

11. The system according to claim 1, in which the filling level sensors are arranged on an inner side wall of the fluid collection bag.

12. The system according to claim 1, in which the filling level sensors are arranged in an area where the pressure is atmospheric or over atmospheric.

13. The system according to claim 1, in which the collected volume of bodily fluids inside the fluid collection bag is prevented from splashing over the filling level sensors during patient transport by means of arranged filling segments in the fluid collection bag.

14. The system according to claim 1, in which evacuated air is released through a filtered and venting mechanism.

15. The system according to claim 14, in which the filtered and venting mechanism is prevented from being occluded by bodily fluid by means of a duck-valve and a welded pattern placed respectively on and/or in said fluid collection bag.

16. The drainage system according to claim 1, further comprising a disposable article, the disposable article comprising the drainage tubing arranged in fluid communication with the pre-chamber.

17. The drainage system according to claim 16, wherein the disposable article further comprises the fluid collection bag and the drainage tubing is connected to the fluid collection bag.

18. The system according to claim 1, wherein the pre-chamber is connected between tubing arranged to be connected to a patient, and at least a portion of the drainage tubing arranged to interact with the peristaltic mechanism.

19. The system according to claim 1, wherein the pre-chamber is provided with the pressure sensor and one or more filling sensors.

* * * * *